United States Patent
Bini et al.

(10) Patent No.: US 7,560,937 B2
(45) Date of Patent: Jul. 14, 2009

(54) MICROWAVE SENSOR FOR MEASURING THE MOISTURE OF MASONRY SURFACES COMPRISING A MICROSTRIP RESONATOR COUPLED WITH AN OPEN COAXIAL PROBE

(75) Inventors: Marco Bini, Pistoia (IT); Amleto Ignesti, Florence (IT); Roberto Olmi, Florence (IT); Lapo Pieri, Florence (IT); Saverio Priori, Florence (IT); Cristiano Riminesi, Florence (IT)

(73) Assignee: Consiglio Nazionale Delle Ricerche, Rome (IT)

( * ) Notice: Subject to any disclaimer, the term of this patent is extended or adjusted under 35 U.S.C. 154(b) by 101 days.

(21) Appl. No.: 11/574,691

(22) PCT Filed: Sep. 2, 2005

(86) PCT No.: PCT/IT2005/000505

§ 371 (c)(1), (2), (4) Date: Mar. 5, 2007

(87) PCT Pub. No.: WO2006/027812

PCT Pub. Date: Mar. 16, 2006

(65) Prior Publication Data
US 2007/0247169 A1   Oct. 25, 2007

(30) Foreign Application Priority Data
Sep. 6, 2004   (IT) ............... FI2004A0187

(51) Int. Cl.
  G01R 27/04   (2006.01)
(52) U.S. Cl. .............. 324/634; 324/632; 324/643
(58) Field of Classification Search .......... 324/634, 324/632, 643
See application file for complete search history.

(56) References Cited

U.S. PATENT DOCUMENTS

| | | | |
|---|---|---|---|
| 5,233,306 A * | 8/1993 | Misra | 324/642 |
| 5,397,993 A | 3/1995 | Tews et al. | |
| 5,541,522 A * | 7/1996 | Rosen et al. | 324/642 |
| 5,900,618 A * | 5/1999 | Anlage et al. | 250/201.3 |
| 6,376,836 B1 | 4/2002 | Anlage et al. | |
| 6,407,555 B2 * | 6/2002 | Joshi et al. | 324/636 |
| 6,614,227 B2 * | 9/2003 | Ookubo | 324/635 |

(Continued)

OTHER PUBLICATIONS

Olmi et al., Non-destructive permittivity measurement of solid materials, 2000, Meas. Sci. Technol. 11, pp 1623-1629.*

(Continued)

*Primary Examiner*—Timothy J Dole
(74) *Attorney, Agent, or Firm*—McGlew and Tuttle, P.C.

(57) ABSTRACT

The measurement device includes a microwave sensor, a microwave analyzer which is essentially composed of a microwave signal generator and a microwave power meter, and a processing unit to which the analyzer is interfaced. The sensor 3 includes a resonator 9 and an open coaxial probe 11. The resonator 9 is produced by means of a length of microstrip line 13, terminating with the probe 11 and short-circuited at one end 13A. The microstrip is produced on a laminate of low-loss dielectric material 15. The collector plate forming the ground is indicated with 17. Operating on the microstrip 13 are two weakly coupled ports with coaxial output, indicated with 19 and 21 respectively.

17 Claims, 3 Drawing Sheets

U.S. PATENT DOCUMENTS 6,809,533 B1 * 10/2004 Anlage et al. ............... 324/750
6,831,470 B2 * 12/2004 Xie et al. ..................... 324/693

OTHER PUBLICATIONS

Zurcher, J. F. et al.; "Nondestructive microwave measurements of materials moisture in building walls"; Measurement for Progress in Science and Technology. Proceedings of the Imeko Congress of the International Measurement Confederation North-Holland Amsterdam, Netherlands, vol. II, 1980, pp. 393-398, XPoo1207707 ISBN: 0-444-85475-4.

Rosner, Bjoern T. et al.; "High-frequency near-field microscopy"; Review of Scientific Instruments, American Institute of Physics, US, vol. 73, No. 7, Jul. 2002, pp. 2505-2525, XP012040085, ISSN: 0034-6748.

Byoungjoong, Kang et al.; "A planar-type probe with a coaxial aperture for nondestructive complex permittivity measurement of biological materials up to 30 GHz"; Microwave Symposium Digest, 2004 IEEE MIT-S Itnernational Forth Worth, TX, USA, Jun. 6-11, 2004, Piscataway, NJ, USA, IEEE, vol. 3, Jun. 6, 2004, pp. 1441-1444, XP010728065, ISBN: 0-7803-8331-1.

Wenger, J. et al.; "An MMIC-based microwave sensor for accurate clearance measurements in aircrafts engines"; 27th European Microwave Conference Proceedings. Jerusalem: Ortra Ltd., IL., vol. 2 of 2, Sep. 8, 1997, pp. 1122-1126, XP001075461, p. 1123, Paragraph 1-Paragraph 2.

Bhimnathwala, H. B. et al.; "A microwave system for high accuracy high spatial resolution dielectric constant uniformity measurement"; Proceedings of the European Microwave Conference. Budapest, Sep. 10-13, 1990, Tunbridge Wells, MEP, GB, vol. 1 Conf. 20, Sep. 10, 1990, pp. 495-500, XP000326994.

* cited by examiner

MICROWAVE SENSOR FOR MEASURING THE MOISTURE OF MASONRY SURFACES COMPRISING A MICROSTRIP RESONATOR COUPLED WITH AN OPEN COAXIAL PROBE

The present invention relates to a sensor to measure significant parameters to perform diagnostics on masonry walls, plasters and other articles also of artistic interest, such as frescoes or the like. More specifically, the present invention relates to a sensor to detect, in articles of the aforesaid type, moisture, the presence of surfacing salts caused by moisture and the like.

The invention also relates to a measurement device including a sensor of the aforesaid type, and to a measurement method for diagnostics on masonry surfaces and the like.

The object of the present invention is to produce a sensor and a measurement instrument employing said sensor, which allows precise and repeatable measurements of the moisture content and of other parameters useful for diagnostic purposes on plasters, masonry walls, frescoes or other articles on which diagnosis is required of the conditions related to the presence of moisture.

Essentially, the invention is based on the principle of measuring the dielectric features of the material by means of the variation of the resonance frequency of a sensor including a resonator, and an open coaxial probe which interfaces the resonator with the outside world through evanescent coupling and forms, together with the resonator, a resonant electromagnetic structure. By applying the open end of the probe to the surface of the article to be analyzed, there is a variation of the capacity values and losses of the probe and, consequently, both of the resonance frequency and the quality factor of the resonant system. It has been found, and the invention is based on this finding, that from the variations of the resonance frequency it is possible to trace, precisely and repeatably, the moisture content of the material being examined. By also using, as information source, the variation of the quality factor it is possible to obtain, by means of the sensor of the invention, further information, such as the presence of surfacing salts on the surface caused by moisture present in the material.

Therefore, according to a first aspect, the subject of the invention is a sensor for diagnostics on masonry surfaces, plasters and the like, in particular to measure moisture, characterized in that it includes a resonator coupled with an open coaxial probe.

According to a further aspect, the subject of the invention is a device including a sensor of the aforesaid type and a control and measurement circuit interfaced to said sensor.

According to a third aspect, the invention relates to a diagnostic method of masonry surfaces, plasters and the like, in particular to measure moisture, characterized by the step of determining at least one parameter for diagnosing the conditions of a material being examined through at least the resonance frequency value of a resonator coupled with an open coaxial probe which is applied to said material.

Further characteristics and advantageous embodiments of the invention are indicated in the appended dependent claims.

The invention shall be better understood by following the description and accompanying drawing which shows a non-limiting practical embodiment of the invention. More specifically, in the drawing.

Figure 1:
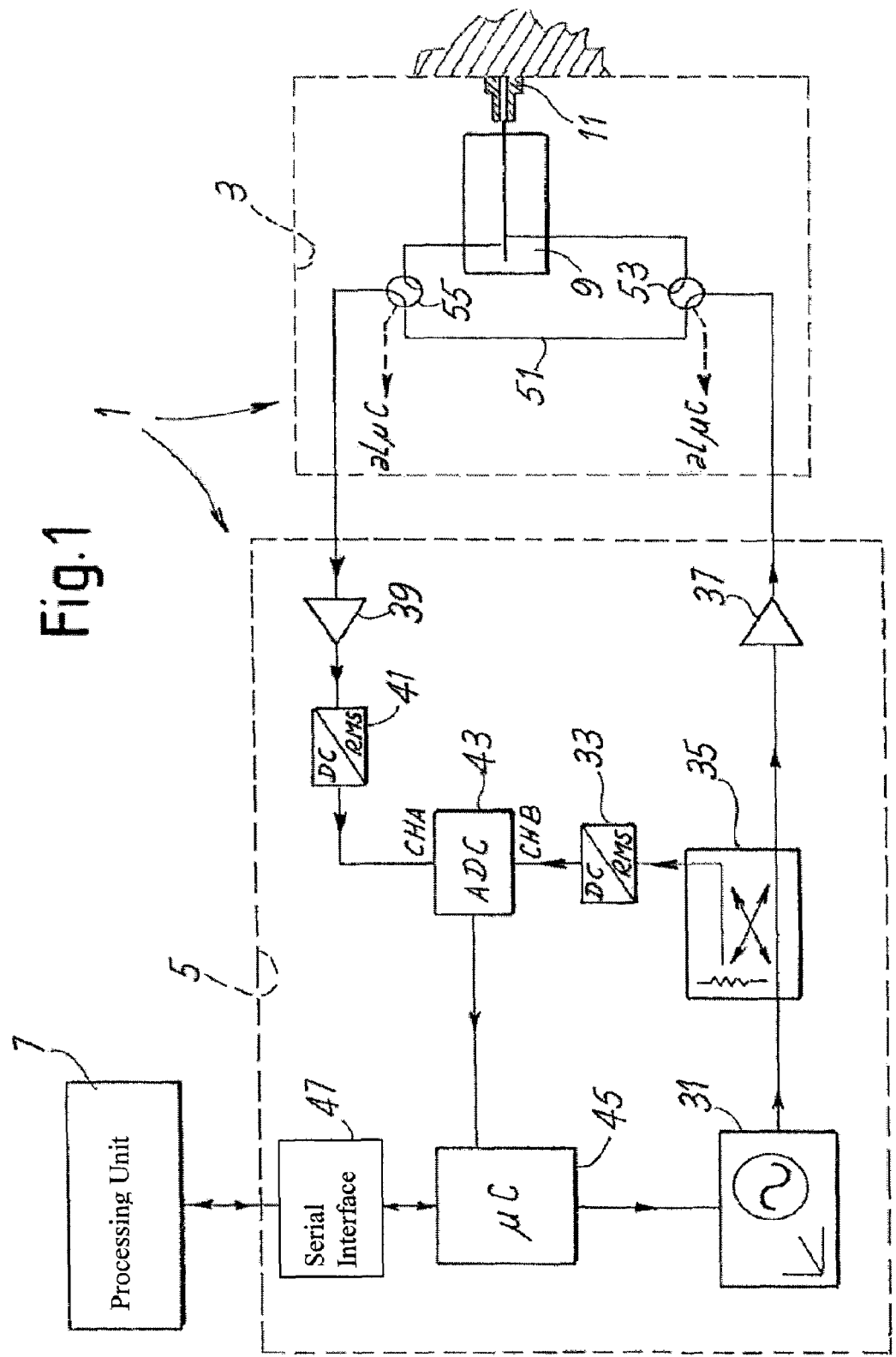
FIG. 1 shows a complete block diagram of the device according to the invention, including a sensor and the microwave analyzer circuit.

With reference to FIG. 1, the measurement device or instrument, indicated as a whole with 1, includes a microwave sensor 3, a microwave analyzer 5 which is essentially composed of a microwave signal generator and a microwave power meter, and a processing unit 7, which can consist, for example, of a personal computer or a lap-top computer to which the analyzer 5 is interfaced.

Figure 2:
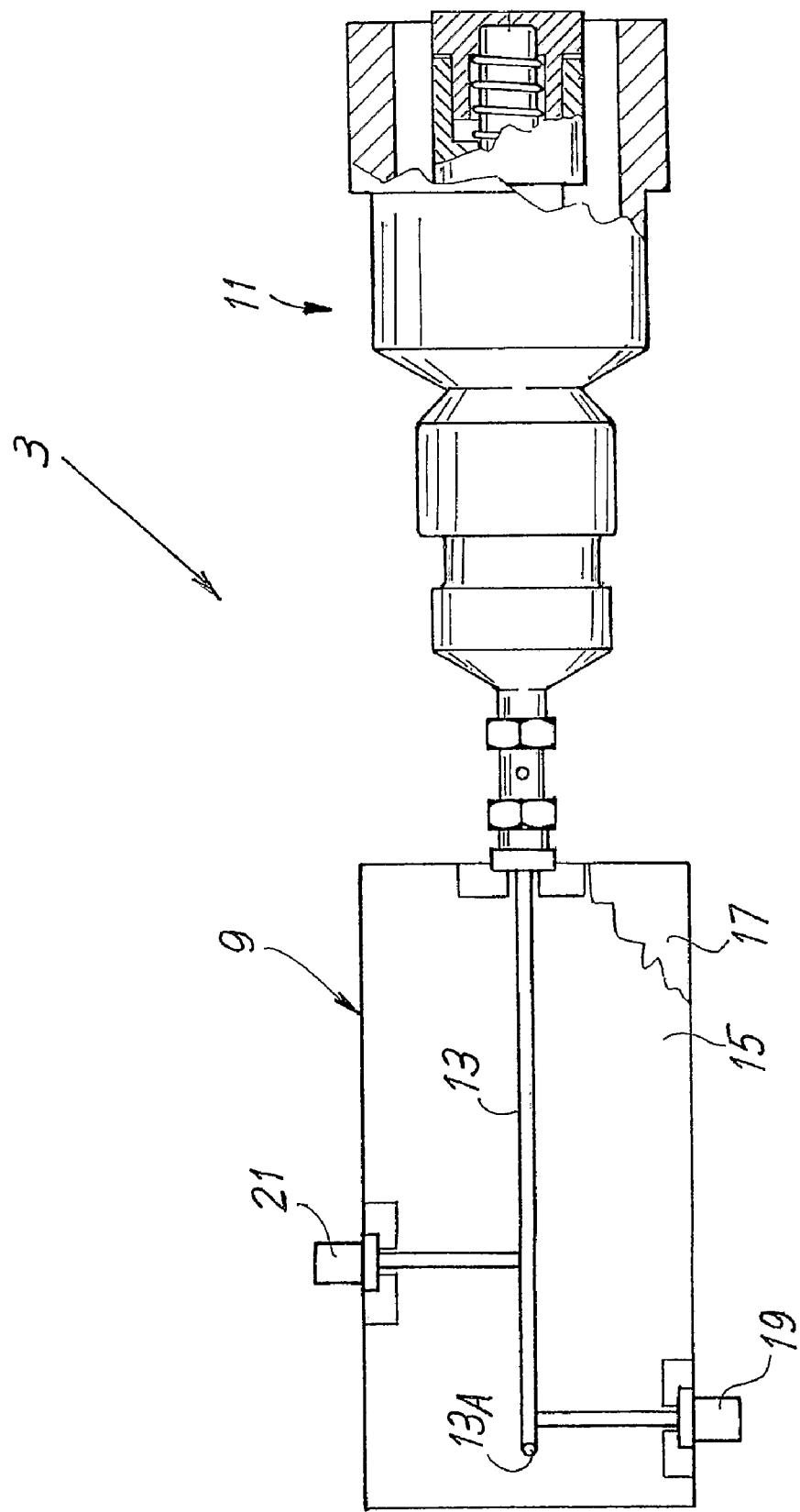
FIG. 2 shows a schematic representation of the sensor.

The sensor 3 includes (see also FIG. 2) a resonator 9 and an open coaxial probe 11. The resonator 9 is produced by means of a length of microstrip line 13, terminating with the probe 11 and short-circuited at one end 13A. The microstrip is produced on a laminate of low-loss dielectric material 15, such as Taconic® 602, with $\in=2.5$, tan $\delta=0.0019$, thickness 1,57 mm. The collector plate forming the ground is indicated with 17. Operating on the microstrip 13 are two weakly coupled (−30 dB) ports with coaxial output, indicated with 19 and 21 respectively.

The probe is produced for example as described in R. Olmi, M. Bini, A. Ignesti, C. Riminesi, <<*Non-destructive permittivity measurement of solid materials*>>, Meas. Sci. Technol. 11 (2000), pagg. 1623-1629, the content of which is incorporated in the present description. It has an elastic central electrode, to allow correct positioning on the surface of the material to be analyzed, as shown schematically in the sectioned portion in FIG. 2.

Figure 3:
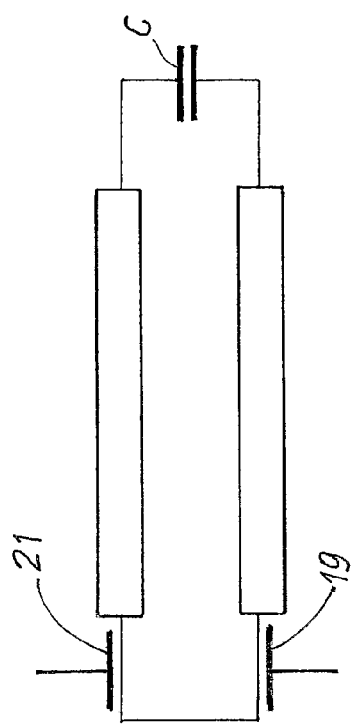
FIG. 3 shows a representative diagram of the equivalent circuit of the sensor according to the invention.

From an electric viewpoint, the sensor can be schematized as shown in FIG. 3. In substance, it is composed of a resonant electromagnetic structure, including a resonator formed by the microstrip 13 with evanescent coupling, by means of the open coaxial probe 11, towards the outside. The capacity C varies according to the material with which the probe 11 is interfaced.

In substance, the equivalent circuit of the resonator in measurement conditions consists of a pair of transmission lines (one for input and the other for output) weakly coupled to a resonant circuit. The resonant circuit is composed of the length of microstrip transmission line, short-circuited at one end and terminating on an impedance with a value linked to the modal structure of the field on the aperture of the coaxial probe. The reflection coefficient on the aperture is obtained by extending in orthogonal modes (TEM and $TM_{0n}$) the field inside the coaxial and expressing the field in the material being measured in terms of magnetic sources on the aperture, by means of the equivalence theorem. Finally, the conditions of continuity allow a system of equations to be obtained in which the unknowns are the reflection coefficients for the infinite modes:

$$\sum_{n=0}^{\infty} \Gamma_n F_n(\varepsilon^*) = 1 \quad (1)$$

where n=0 indicates the mode TEM and $F_n$ are known functions of the complex permittivity of the material being analyzed. For tan $\delta$ values up to a few tenths, the solution of the problem can be simplified by separating the measurement of $\in'$ from that of tan $\delta$. In these conditions, in fact, the resonance frequency is independent from the imaginary part of $\in^*$ or, in other words, the termination impedance of the resonator in which said glue is a hotmelt glue is capacitive. From the resonance condition:

$$Z_c \tan(\beta_0 D) = \frac{1}{\omega_r C(\varepsilon')} \tag{2}$$

the capacity $C(\varepsilon')$ is obtained and, calculating the reflection coefficient $\Gamma_0$ by means of (1), the value of $\varepsilon'$ which satisfies (4) is finally obtained. In (2) and (3) $Z_c$ is the characteristic impedance of the two lines in cascade (microstrip and coaxial, both 50 $\Omega$), D is the equivalent length in air of the resonant structure and $\beta_0$ is the wavenumber in air:

$$j\omega_r C(\varepsilon') = \text{Im}\left(\frac{1-\Gamma_0}{1+\Gamma_0}\right)\frac{1}{Z_c} \tag{3}$$

The smallness of the ratio between the volume affected by the evanescent field and the total volume of the resonant structure justifies a perturbative approach for the calculation of tan $\delta$. The relative variation of the complex frequency $\overline{\omega} = \omega(1+j/2Q)$ is proportional to the relative variation of permittivity, with the proportionality coefficient depending on the geometry ($K_g$) and on the aforesaid volume ratio;

$$\frac{\Delta\overline{\omega}}{\overline{\omega}} = -K_g \frac{\Delta v}{v}\frac{\Delta\varepsilon^*}{\varepsilon^*} \tag{4}$$

where v is the total volume which determines resonance and $\Delta v$ is the volume in which, during measurement, the dielectric constant changes with respect to the resonance in air.

By equalizing the real and imaginary parts of the two members of (4), and disregarding $(\omega/2Q)^2$ with respect to $\omega^2$, the following expression is finally obtained for tan $\delta$:

$$\tan\delta = \frac{\omega_r}{2\varepsilon'}\frac{\varepsilon'-1}{\omega_{r0}-\omega_r}\left(\frac{1}{Q}-\frac{1}{Q_0}\right) \tag{5}$$

(5) is calculated on the basis of the variation of the resonance frequency in air ($\omega_{r0}$) and on the material ($\omega_r$). As expected, tan $\delta$ is inversely proportional to the quality factor due to the material (inverse of the difference between total $Q^{-1}$ and unloaded $Q_0^{-1}$).

The link between permittivity and moisture content in hygroscopic materials is known. The presence of this link, even if difficult to quantify exactly, suggests that it is possible to evaluate the Moisture Content (MC) in a material on the basis of measurement of the dielectric properties thereof. The possibility of rigorously linking, from a theoretic viewpoint, permittivity and moisture content is somewhat remote and would in any case depend greatly on the type of material and the way in which water is captured therein and released therefrom. It nonetheless appears plausible, and is generally accepted at least as a first approximation, that the link between the MC($\Psi$) and the permittivity $\varepsilon'$-j$\varepsilon''$ of the material is of the type:

$$A(\psi) = \frac{\varepsilon'-1}{\varepsilon''} \tag{6}$$

The ratio A($\Psi$) is more or less independent of the density of the material. The specific form of this link depends on the type of material, the measurement frequency and the range of values of the moisture content of interest. It is therefore possible to determine a function of the complex permittivity which provides an estimate of the moisture content of a material.

Assuming that the ratio (6) constitutes a measurement of the inverse of the moisture content, the results of the previous mathematical treatment show how a simple measurement of the relative variation of the resonance frequency ($\Delta\omega_r/\omega_r$) and of the absolute variation of the inverse of the quality factor $Q^{-1}$ (that is, $\Delta 1/Q$) of the sensor applied to a material to be analyzed with respect to the same parameters in air are able to provide an estimate of the moisture, without the need (and burden) to calculate $\varepsilon^*$.

Taking into account that by definition $$\tan\delta = \varepsilon''/\varepsilon'$$

it in fact ensues from (5) and (6) that:

$$A(\psi) = \frac{\Delta\omega_r}{\omega_r}\frac{2}{\Delta\frac{1}{Q}} \tag{7}$$

Therefore, with the sensor described above, by evaluating the variation of the resonance frequency of the system composed of the probe and of the resonator, and the variation of the quality factor of said system, it is possible to obtain information on the conditions of moisture content of the material, as well as other useful information such as the presence of surfacing salts on the surface.

For this purpose the sensor described hereinbefore is controlled and managed by the circuit of the device shown schematically in FIG. 1 and already partly described. Again with reference to FIG. 1, the circuit 5 includes a frequency synthesized signal generator 31, with a sufficiently constant amplitude, which controls the sensor and the signal of which is sent, by means of a directional coupler 35, also to a detector 33 for level control. In this way the amplitude of the signal directed towards the sensor 3 is measured with precision and allows significant accuracy of level detection on the entire the frequency range.

Before being sent to the sensor 3, the signal is made to pass through an amplifier 37 with the dual purpose of raising the level, given the high attenuation of the sensor complex, and of separating the sensor from the signal generation part.

With regard to the measurement part, the signal picked up by the resonant structure of the sensor is first amplified by means of an amplifier 39 to recover a little more of the attenuation of the sensor complex 3 and is then sent to a true RMS converter 41 which provides, at the output thereof, a continuous signal proportional to the radiofrequency power present at the input thereof. Given the availability on the market of integrated detectors with high dynamics (over 50 dB), it is not necessary to implement frequency conversions or automatic level control systems which would have made the entire system more complex and costly and have required more complex calibration mechanisms, both during manufacture and by the user.

The continuous signal representing the power measured at the output of the sensor is sent to an analog/digital converter 43 with suitable resolution. This converter and all the other stages (synthesizer, switches in the sensor) are controlled by a microcontroller system 45 which also interfaces the circuit with the outside, although processing is left to the more powerful calculation unit 7 which is external to this subsystem 5. Interfacing with the calculation unit 7 is obtained by means of a serial interface 47. This serial interface guarantees sufficient speed in transferring data and can also be implemented on all future calculation units provided for this measurement system.

The instrument has the highest possible level of integration, in order to minimize both production costs and the costs of factory adjustment. In the same way, all the parts are given the necessary strength to withstand operating conditions and stresses (thermal, mechanical and aging), and calibration and operational check procedures capable of detecting, to as great an extend possible, any malfunctioning (for example, caused by damage) of the instrument. For this purpose, as schematized in FIG. 1, the sensor is provided with a calibration path 51 between the input and the output of the signal, associated with two switches 53, 55 controlled by the microcontroller 45.

Figure 4:
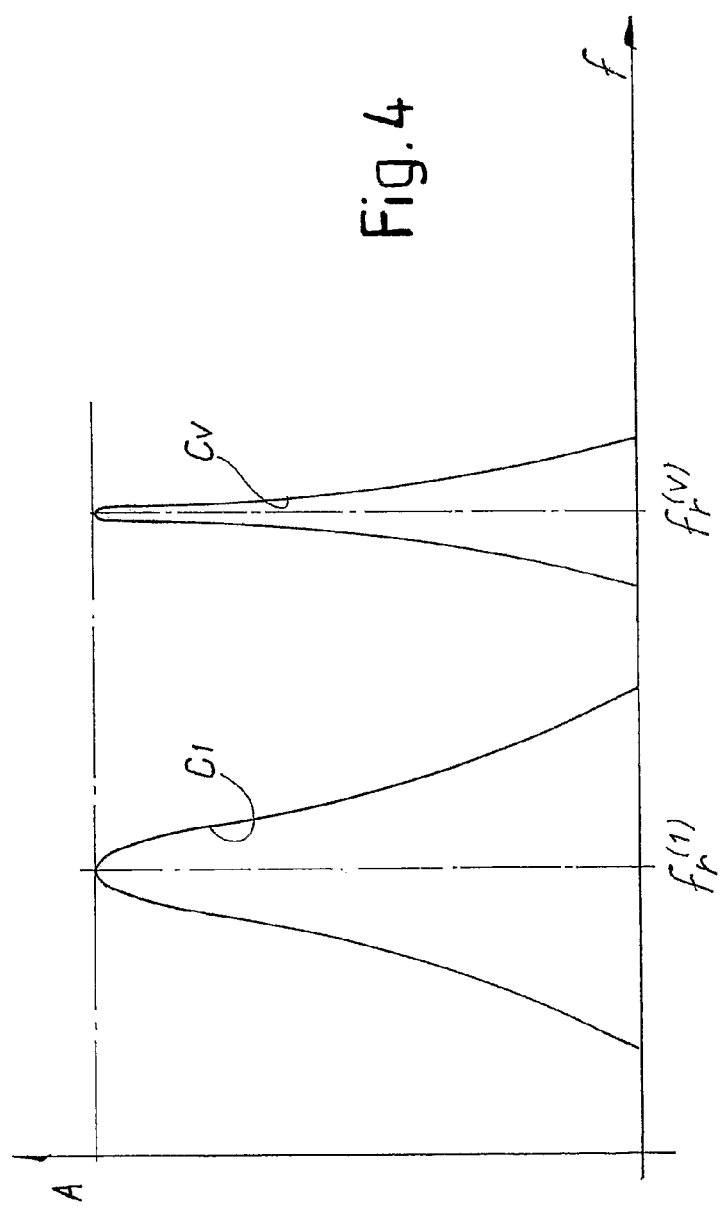
FIG. 4 shows a chart representing the variation of the resonance frequency and quality factor of the sensor caused by the presence of the material to be analyzed.

The measurement procedure consists in calibration in air from which the electrical length D of the resonant structure and the unloaded quality factor Q are obtained, followed by a measurement on the material. In both cases, the entire resonance curve is acquired, from which the parameters of interest are then extracted: the resonance frequency $f_r$ and the bandwidth $\Delta f$, from which the $Q=f_r/\Delta f$ is obtained. FIG. 4 schematically shows the unloaded resonance curve Cv, that is, in air, and a resonance curve C1 obtained by applying the sensor to the material to be analyzed. It can be seen that the presence of the material in front of the coaxial probe causes a reduction in the resonance frequency from fr(v) to fr(1) and a widening of the band, that is, a decrease in the quality factor. These two data can be correlated to the moisture content in the material and also to other factors, such as the presence of surfacing salt crystals on the surface of the material as a result of moisture.

Typically, by using a sensor with a known frequency in air, during measurement it is controlled with a variable frequency in an amplitude range of approximately 15% and in any case preferably no more than 30% of the value of the resonance frequency in air of said sensor. As the presence of the material to be analyzed causes a decrease in the resonance frequency with respect to the frequency in air, the measurement range will be positioned above the resonance frequency in air.

The frequencies of interest for this type of sensor typically range from 100 MHz to 10 GHz.

The measurement method was validated on various materials with known properties, such as teflon, stycast k12, Ampex ATD80, paper and various species of wood (fir, pine, oak, chestnut, poplar). Calibration in air indicates that the resonant electromagnetic structure used has the following characteristics when unloaded: f0=1.19 GHz, Q0=179.7, D=0.186 m. The measurements are indicated in Table 1. The measurement method has a high resolving power: for example, a variation of approximately 1.3 of the dielectric constant reflects in a movement in frequency of over 10 MHz.

| Material | $f_r$ (GHz) | Q | $\epsilon'$ | tan$\delta$ |
|---|---|---|---|---|
| teflon | 1.173 | 178.6 | 2.1 | $6 \times 10^{-4}$ |
| sty. k12 | 1.061 | 113.4 | 11.0 | $1 \times 10^{-2}$ |
| atd80 | 0.862 | 115.1 | 83.5 | $4 \times 10^{-3}$ |
| paper | 1.170 | 89.8 | 2.4 | $9 \times 10^{-2}$ |
| fir | 1.168 | 74.4 | 2.5 | 0.12 |
| chestnut | 1.170 | 63.0 | 2.4 | 0.16 |
| pine | 1.180 | 118.0 | 1.7 | $6 \times 10^{-2}$ |
| poplar | 1.176 | 98.6 | 2.0 | $8 \times 10^{-2}$ |
| oak | 1.170 | 58.5 | 2.4 | 0.18 |

It is understood that the drawing only shows a practical embodiment of the invention, the forms and arrangements or which may vary without however departing from the scope of the concept on which the invention is based, as defined in the appended claims.

The invention claimed is:

1. A sensor for diagnostics on masonry surfaces, comprising:
   a resonator coupled with an open coaxial probe, said resonator including a length of microstrip line, said length of microstrip line and said open coaxial probe forming a resonant electromagnetic structure with evanescent coupling, said microstrip being provided with a first port for signal input and a second port for signal output, said first port and said second port being weakly coupled to said microstrip, said microstrip being short-circuited at one end and connected to said probe at an opposite end.

2. Sensor as claimed in claim 1, wherein said first and second port have a coaxial output.

3. Sensor as claimed in claim 2, wherein said coaxial probe includes an elastic central electrode, to allow correct positioning on a surface of a material to be analyzed.

4. Sensor as claimed in claim 1, wherein said coaxial probe includes an elastic central electrode, to allow correct positioning on a surface of a material to be analyzed.

5. Sensor as claimed in claim 1, wherein said microstrip is short-circuited at one end and associated with two weakly coupled ports with coaxial output.

6. Sensor as claimed in claim 1, further comprising a resonant setting device, to vary the resonance frequency in air of the resonator.

7. Sensor as claimed in claim 6, wherein said microstrip is short-circuited at one end and associated with two weakly coupled ports with coaxial output and said length of microstrip line is interchangeable to vary the resonance frequency in air of the resonator.

8. Sensor as claimed in claim 1, wherein said resonator has a resonance frequency in air ranging from 100 MHz to 10 GHz.

9. A device for diagnostics on masonry surfaces, comprising:
   a sensor; and
   a control and measurement circuit associated with an input and an output to said sensor, said sensor comprising a resonator coupled with an open coaxial probe, said resonator including a length of microstrip line, said length of microstrip line and said open coaxial probe forming a resonant electromagnetic structure with evanescent coupling, said microstrip being provided with a first port for signal input and a second port for signal output, said first port and said second port being weakly coupled to said microstrip, said microstrip being short-circuited at one end and connected to said probe at an opposite end.

10. Device as claimed in claim 9, wherein said circuit includes a microwave sender to send a variable frequency microwave signal to said sensor and to detect at least the resonance frequencies of the sensor applied to a material to be analyzed.

11. Device as claimed in claim 10, further comprising a detector to determine the bandwidth of the resonant system formed by the sensor and by the material to be analyzed.

12. Device as claimed in claim 11, further comprising a device to determine the quality factor of said resonant system.

13. Device as claimed in claim 9, wherein said control and measurement circuit includes:
   a microcontroller;
   a frequency synthesized signal generator, the signal of which controls the sensor;
   a true RMS converter, connected to the output of the sensor;
   an analog/digital converter, the input of which receives the signal output by the true RMS converter; and
   a circuit interfacing with an external processing unit.

14. Device as claimed in claim 13, further comprising a detector to control the level of signal of said signal generator, connected at the output from the signal generator by means of a directional coupler.

15. Device as claimed in claim 9, wherein said control and measuring circuit is designed to excite the sensor with a signal having a frequency variable within a range equal to or less than 30% of the resonance frequency in air of the sensor, below said resonance frequency in air.

16. Device as claimed in claim 9, wherein said control and measuring circuit is designed to determine, by means of measurement of the resonance frequency and/or of the quality factor of the resonator interfaced to the material being analyzed, one or more of the following conditions: presence and degree of moisture; presence of salts; surface roughness.

17. Device as claimed in claim 9, wherein said coaxial probe includes an elastic central electrode, to allow correct positioning on a surface of a material to be analyzed.

* * * * *